United States Patent
Rego et al.

(10) Patent No.: US 11,253,623 B2
(45) Date of Patent: *Feb. 22, 2022

(54) METHOD AND APPARATUS FOR PROVIDING POLYIODIDE RESIN POWDER-ENHANCED PERSONAL PROTECTIVE EQUIPMENT (PPE)

(71) Applicant: Valencide LLC, San Diego, CA (US)

(72) Inventors: Albert Rego, Mission Viejo, CA (US); Lynn R. Detlor, Ramona, CA (US); Aileen Law, Denver, CO (US)

(73) Assignee: VALENCIDE LLC

( * ) Notice: Subject to any disclaimer, the term of this patent is extended or adjusted under 35 U.S.C. 154(b) by 0 days.

This patent is subject to a terminal disclaimer.

(21) Appl. No.: 17/141,961

(22) Filed: Jan. 5, 2021

(65) Prior Publication Data

US 2021/0128767 A1   May 6, 2021

Related U.S. Application Data

(63) Continuation-in-part of application No. 17/008,341, filed on Aug. 31, 2020, now Pat. No. 11,071,975,
(Continued)

(51) Int. Cl.
*A61L 2/232* (2006.01)
*C08L 27/10* (2006.01)
(Continued)

(52) U.S. Cl.
CPC .............. *A61L 2/232* (2013.01); *B41M 1/10* (2013.01); *C08L 27/10* (2013.01); *A61L 2101/46* (2020.08); *A61L 2300/404* (2013.01)

(58) Field of Classification Search
CPC ...................................................... A61L 2/232
See application file for complete search history.

(56) References Cited

U.S. PATENT DOCUMENTS

| | | |
|---|---|---|
| 4,010,259 A | 3/1977 | Johansson |
| 4,381,380 A | 4/1983 | LeVeen et al. |

(Continued)

FOREIGN PATENT DOCUMENTS

| | | |
|---|---|---|
| WO | 2010033258 A1 | 3/2010 |
| WO | 2010124130 A2 | 10/2010 |

OTHER PUBLICATIONS

Yue et al (Adv. Funct. Mater. 2015, 25, 6756-6767). (Year: 2015).*

(Continued)

*Primary Examiner* — Benjamin J Packard
(74) *Attorney, Agent, or Firm* — Aileen Law; Oppedahl Patent Law Firm LLC (57) ABSTRACT

Disclosed is a method and apparatus for providing polyiodide resin-enhanced personal protective equipment (PPE) including but not limited to face masks, gloves, gowns and respirators. The disclosed method comprises the application of a polyiodinated ink polymer in or on one or more targeted surfaces of PPE to create a molecular sub-microscopic protective barrier between the equipment and the user. The disclosed system provides a PPE device capable of direct contact kill of organisms. In addition, the system provides for a sustained kill of organisms for up to 96 hours. The resultant PPE device is broadly effective against viral, bacterial, fungicidal and other microbial agents.

21 Claims, 4 Drawing Sheets

Figure 1:
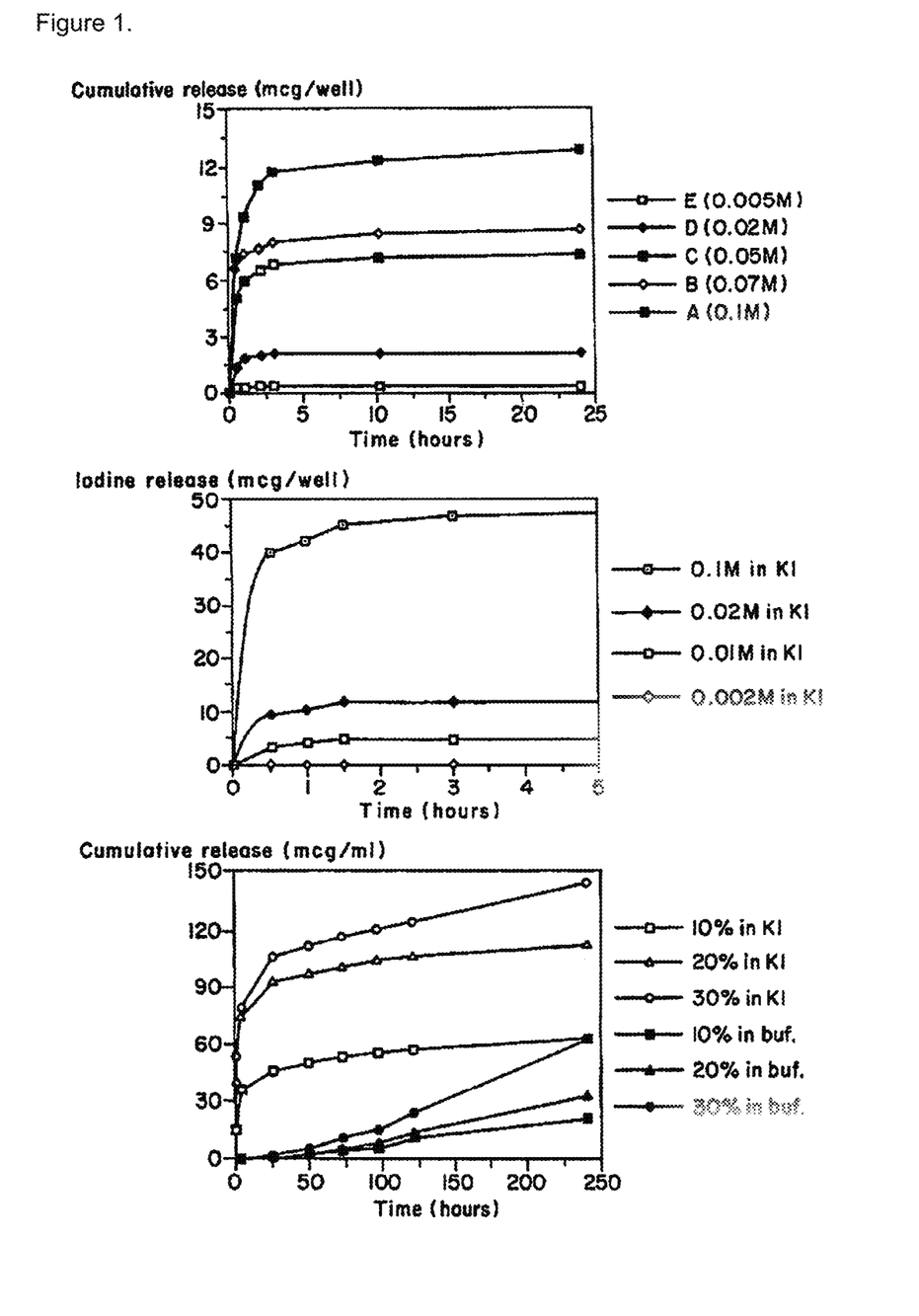
Figure 2:
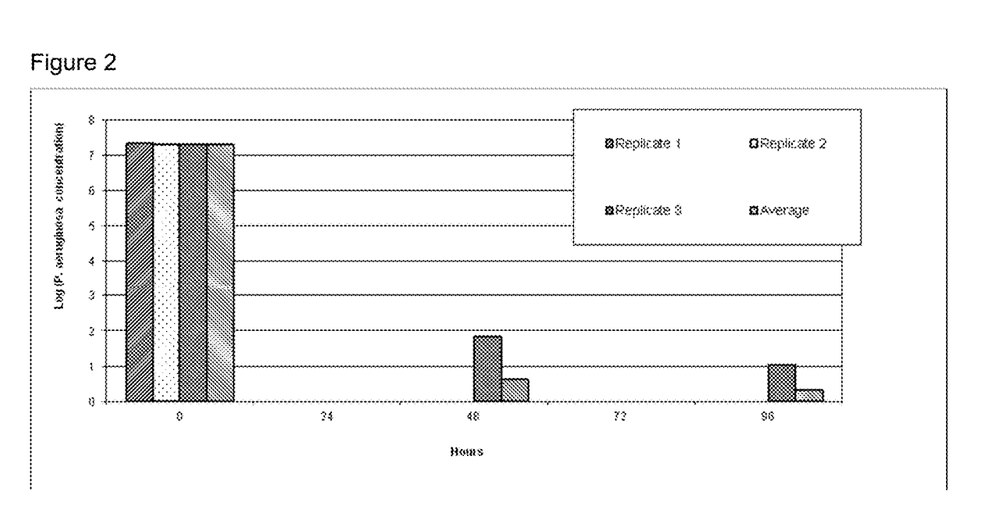
Figure 3:
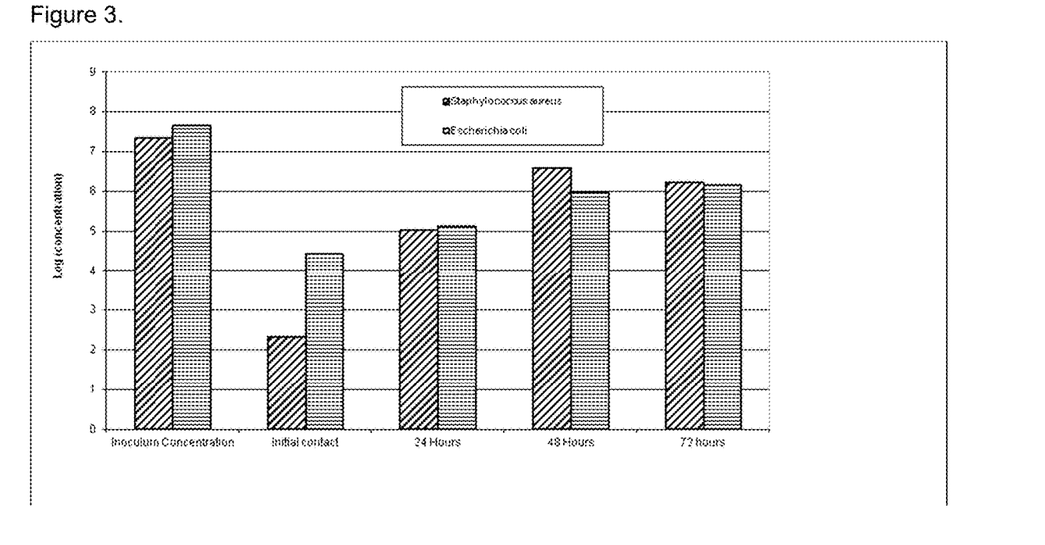
Figure 4:
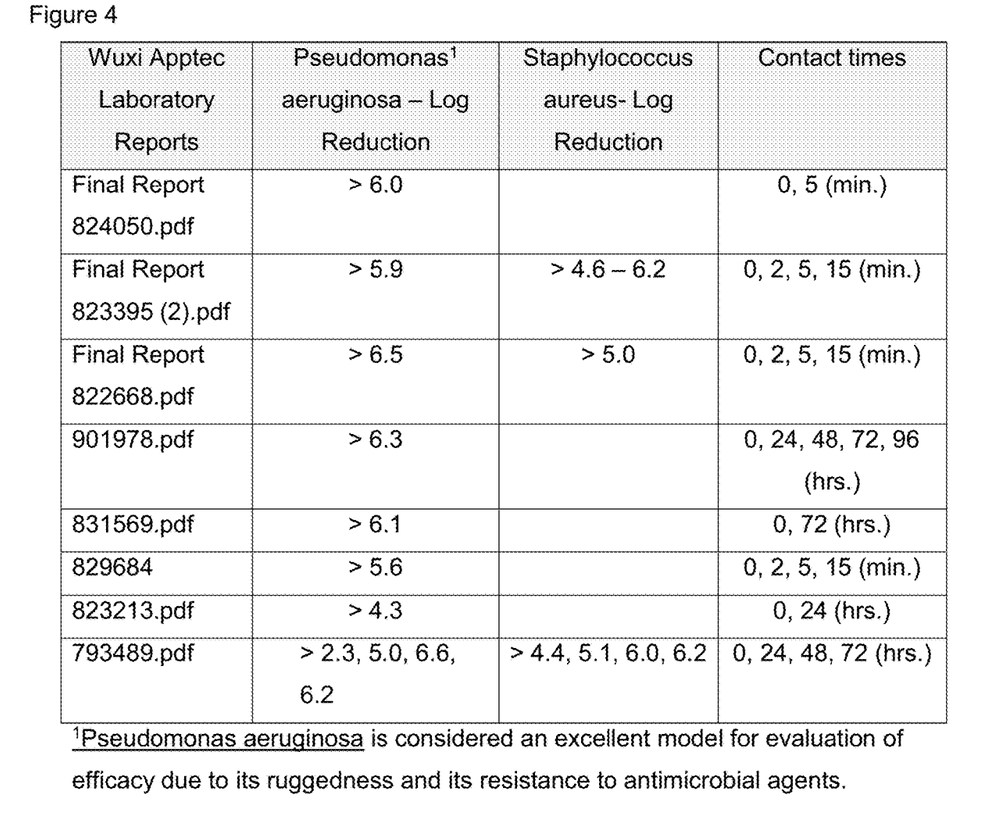

Related U.S. Application Data which is a continuation-in-part of application No. 16/844,967, filed on Apr. 9, 2020, now Pat. No. 10,758,480, which is a continuation-in-part of application No. 15/711,424, filed on Sep. 21, 2017, now Pat. No. 10,709,819.

(51) Int. Cl.
  *B41M 1/10* (2006.01)
  *A61L 101/46* (2006.01)

(56) References Cited

U.S. PATENT DOCUMENTS

| | | | |
|---|---|---|---|
| 4,999,190 A | | 3/1991 | Fina |
| 2014/0217037 A1* | | 8/2014 | Theivendran .......... B01J 47/016 |
| | | | 210/753 |

OTHER PUBLICATIONS

Dolez (JOSE 2009, vol. 15, No. 4). (Year: 2009).*
Luo et al., "Antimicrobial Activity and Biocompatibility of Polyurethane-Iodine Complexes." Journal of Bioactive and Compatible Polymers, vol. 25, No. 2, Mar. 2010, pp. 185-206.

* cited by examiner

| Wuxi Apptec Laboratory Reports | Pseudomonas[1] aeruginosa – Log Reduction | Staphylococcus aureus- Log Reduction | Contact times |
|---|---|---|---|
| Final Report 824050.pdf | > 6.0 | | 0, 5 (min.) |
| Final Report 823395 (2).pdf | > 5.9 | > 4.6 – 6.2 | 0, 2, 5, 15 (min.) |
| Final Report 822668.pdf | > 6.5 | > 5.0 | 0, 2, 5, 15 (min.) |
| 901978.pdf | > 6.3 | | 0, 24, 48, 72, 96 (hrs.) |
| 831569.pdf | > 6.1 | | 0, 72 (hrs.) |
| 829684 | > 5.6 | | 0, 2, 5, 15 (min.) |
| 823213.pdf | > 4.3 | | 0, 24 (hrs.) |
| 793489.pdf | > 2.3, 5.0, 6.6, 6.2 | > 4.4, 5.1, 6.0, 6.2 | 0, 24, 48, 72 (hrs.) |

[1]Pseudomonas aeruginosa is considered an excellent model for evaluation of efficacy due to its ruggedness and its resistance to antimicrobial agents.

METHOD AND APPARATUS FOR PROVIDING POLYIODIDE RESIN POWDER-ENHANCED PERSONAL PROTECTIVE EQUIPMENT (PPE)

TECHNICAL FIELD

The present disclosure relates to an agent comprising polyiodide resin for use with devices such as face masks, surgical masks, caps, isolation gowns, shoe covers, surgical drapes, gloves, respirators and other personal protective equipment (PPE) and the like to provide or facilitate an immediate contact kill of bacteria, fungi and viruses. More specifically, the present method and apparatus provides for use of a bactericidal, fungicidal and virucidal agent for infections such as tuberculosis, "SARS" caused by the SARS-coronavirus (SARS-CoV or SARS-CoV-1), "MERS" caused by the MERS-coronavirus (MERS-CoV) and "COVID-19" caused by the SARS-coronavirus (SARS-CoV-2), influenza viruses and ebolaviruses affecting the lungs of a mammal.

BACKGROUND

Iodine is a well-known broad spectrum antimicrobial agent that has bactericidal, fungicidal and virucidal properties which has been used for over centuries as an antiseptic. When iodine is introduced into an aqueous solution, free iodine, which provides the germicidal effect, is released. While generally inhibiting infective germs over the short term, the biocidal effectiveness of iodine is dependent on, inter alia, how long the infective agent is exposed to it.

To increase the effectiveness of iodine, it is normally combined with a solubilizing agent or other carrier to form an iodophor. Such iodophors, in effect, provide a reservoir of iodine from which small amounts of free iodine in aqueous solution are released over a period of time. This iodophor formulated for example, as a solution, soap, cream or paste, and are then topically applied to that area of a patient's body which is desired to be treated. Perhaps the best known of these iodophors is povidone-iodine, in which iodine in the form of triiodide is complexed with the polymer polyvinylpyrrolidone. An example of such an application can be found by reference to U.S. Pat. No. 4,010,259.

Polyiodide resins have proven to be as much as 1,000,000 times more effective than an iodine ($I_2$) molecule alone. A large number of chemical, biochemical, and physiological studies have proven that the iodine added to microorganisms is irreversibly bound. This has the effect of devitalizing the microorganisms by damaging cellular proteins, lipids, enzymes, oxidation of sulfhydryl groups and other chemical pathways.

Microorganisms carry an electrical potential energy on their surface. The polyiodide resin carries an electrical potential charge which attracts the microorganisms. The microorganisms with their negative electrical potential are naturally drawn to the iodinated resin particles with their positive electrical potential charge and vice versa, thus ensuring contact and devitalization. The iodinated resin releases the correct lethal dose of nascent iodine in less than about 3 seconds at a body temperature of about 98.6° C. or about 36.9° C.

The ion-exchange resin bead or particle is chemically bonded homogeneously with polyiodide of uniform composition throughout its interior. As nascent iodine is consumed more is continuously fed to the surface from the interior of the resin bead or particle.

This creates an equilibrium of the resin 13 to the natural release of 12 into the immediate environment as follows:

$$Resin\text{-}I_3 \leftrightarrow Resin\text{-}I^- + I_2$$

$$Resin\text{-}I_5 \leftrightarrow Resin\text{-}I_3 + I_2 \leftrightarrow Resin\ I^- + I_2 + I_2$$

$$Resin\text{-}I_7 \leftrightarrow Resin\ I_5 + I_2 \leftrightarrow Resin\ I_3 + I_2 + I_2 \leftrightarrow Resin\ I^- + I_2 + I_2 + I_2$$

By enabling effective disinfection and/or sterilization of the immediate environment at or on the surface of a target apparatus, the disclosed method and device provides a zone of inhibition as a protective barrier around the corresponding PPE. This provides for a molecular sub-microscopic "cloud of protection" between the equipment and the user.

The unique release on demand feature of polyiodide resin can be demonstrated by adding resin beads to the well of a depression microscope slide with a suspension of the highly Motile Ciliate Tetrahymena Pyriforms. When observed microscopically, individual cells maintain their motion while swimming in a solution with 2 ppm of iodine residual. However after a collision with a resin bead, their activity dramatically slows and within seconds stops altogether.

Bacteria, viruses, yeast, fungi, and protozoa are not able to develop resistance to iodine even after a period of prolonged exposure to polyiodinated resins. It is not expected that emerging new infections will develop resistance to iodine, as historically there has been no development of resistance to iodine, as well as polyiodinated resin.

What is needed are apparatus capable of providing reliable protection for essential and front line workers, namely those persons who conduct services that are deemed essential to continued critical infrastructure viability. The industries supported by such persons include, but are not limited to, medical and healthcare, telecommunications, information technology systems, defense, food and agriculture, transportation and logistics, energy, water and wastewater, law enforcement, and public works. The disclosed method and device provides a solution to the aforementioned issue. In short, the disclosed method and device provides for a polyiodide resin-enhanced apparatus that utilizes print application methodology to create a molecular sub-microscopic "cloud of protection" between the equipment and the user.

SUMMARY OF THE DISCLOSURE

The disclosed device provides for a polyiodide resin-enhanced apparatus which creates a molecular sub-microscopic "cloud of protection" between the apparatus and the user.

The disclosed device provides for a polyiodide resin-enhanced apparatus that utilizes print application methodology to create a zone of inhibition or a protective barrier around the corresponding PPE.

The disclosed device comprises the application of a polyiodinated ink polymer to one or more surfaces of a respective personal protective device or PPE.

The disclosed device comprises the application of a polyiodinated ink polymer to one or more surfaces of PPE including but not limited to face masks, a surgical masks, caps, isolation gowns, shoe covers, surgical drapes, gloves, respirators and the like using an intaglio printing process.

The disclosed method provides for a polyiodide resin-enhanced apparatus which creates a molecular sub-microscopic "cloud of protection" between the apparatus and the user.

The disclosed method utilizes print application methodology to create a zone of inhibition or a protective barrier around a resultant PPE device.

The disclosed method comprises the application of a polyiodinated ink polymer to one or more surfaces of a respective personal protective device or PPE.

The disclosed method comprises the application of a polyiodinated ink polymer to one or more surfaces of PPE including but not limited to face masks, a surgical masks, caps, isolation gowns, shoe covers, surgical drapes, gloves, respirators and the like using an intaglio printing process.

The disclosed method provides for an imprinted coating of polyiodide resin powder on one or more surfaces of PPE.

The disclosed method provides for an imprinted coating of polyiodide resin powder in one or more surfaces of PPE.

The disclosed system creates a protective polyiodide barrier around a resultant PPE device so as to eliminate the risk of a user contracting pneumonia originating from bacterial, fungal and viral agents.

The disclosed system creates a molecular sub-microscopic "cloud of protection" from bacterial, fungal and viral agents.

The disclosed system provides a PPE device capable of direct contact kill of organisms.

The disclosed system provides for a PPE device capable of sustained kill of organisms for up to 96 hours.

The disclosed system provides for a PPE device having broad viral, bacterial, fungicidal and antimicrobial effectiveness against bacteria, viruses, yeast, fungi, and protozoa.

The disclosed system comprises the application of an agent (polyiodide resin powder) to PPE to facilitate an immediate contact kill of bacteria, fungi and viruses that cause respiratory tract infections affecting the lungs of a mammal.

The disclosed device is applicable to protecting users against various forms of respiratory tract infections, e.g., tuberculosis, pneumonia caused by coronaviruses such as SARS-CoV-1, SARS-CoV-2, MERS-CoV, H1N1 influenza viruses such as SIV or S-OIV and ebolaviruses such as EBOV.

The disclosed method provides for a PPE device capable of protecting its user against various forms of respiratory tract infections, e.g., tuberculosis, pneumonia caused by coronaviruses such as SARS-CoV-1, SARS-CoV-2, MERS-CoV, H1N1 influenza viruses such as SIV or S-OIV and ebolaviruses such as EBOV.

BRIEF DESCRIPTION OF THE FIGURES

FIG. 1. Release rates from previous studies.

FIG. 2 Graph showing biological performance of latex/iodinated resin coated latex elastomers of the present disclosure against the challenge microorganism *Pseudomonas aeruginosa*, with re-inoculation every twenty-four hours (Report Number 901978).

FIG. 3 Graph showing biological performance of latex/iodinated resin coated latex elastomers of the present disclosure against the challenge microorganisms *S. aureus* and *E. Coli* (Report Number 793489).

FIG. 4 Table of compiled data exhibiting contact times and effectiveness.

DETAILED DESCRIPTION OF THE DISCLOSURE

Definitions

Polyiodide—Molecular iodide of more than one iodine atom containing a net negative charge Antimicrobial—An agent that kills microorganisms or inhibits their growth.

Ion-Exchange—An exchange of ions between two electrolytes or the exchange of ions of the same charge between an insoluble solid and a solution in contact with it or an electrolyte solution and a complex or solid state material.

Biological Buffer—An organic substance that has a neutralizing effect on hydrogen ions.

Rotogravure (or gravure for short)—A type of intaglio printing process which involves engraving an image onto an image carrier.

The antitoxic agent disclosed herein—namely, polyiodinated resin particles—act as an antimicrobial agent, an antiviral agent, a biochemical agent or a reducing agent which exerts a toxic effect on a diverse array of microorganisms and other pathogens and environmental toxins while not being toxic to the user. Also disclosed herein is the method of applying a polyiodinated ink polymer comprising polyiodide resin powder of the present device to one or more surfaces of a respective personal protective device or PPE by means of an intaglio printing process.

One having ordinary skill in the art of deposition technologies will recognize that depending on the particular application, other processes could be suitable and modified for adaptability with the apparatus described herein. For example, it is contemplated that current techniques of 3D printing may be used to deposit the iodinated polymer ink as disclosed, as well as offset lithography, flexography, digital printing, large format printing, screen printing, LED UV printing, etc.

Disinfectants are known in the art. One demand disinfectant is polyiodinated resins. The particle sizes of the powders range from about 1 micron to about 150 microns. In some embodiments, the particle sizes range from about 5 microns to about 10 microns. Alternative sources of the polyiodinated resins may be used subject to meeting the same purity and physical conditions. Iodinated resins used in accordance with the present disclosure are referred to as polyiodinated resin.

The base polymer used to manufacture such polyiodinated resins is a strong base anion exchange resin. These resins contain quaternary ammonium exchange groups which are bonded to styrene divinylbenzene polymer chains. Polyiodinated resins can be made with different percentages of iodine and may be used in accordance with the present disclosure. Different percentages of iodine in the polyiodinated resins will confer different properties to the resin, in particular, different levels of biocidal activity. The particular resin used is based on the desired application.

A significant advantage of the present disclosure is that a relatively small amount of the antimicrobial agent need be applied in order to exert a significant toxic effect on a broad spectrum of pathogens.

With regards to efficacy, the present system has been tested against a robust organism *Pseudomonas aeruginosa* utilizing the following recognized standards: AATCC Method 100 (modified for twenty-four hour repeat insult testing) and ASTM E2149 (modified for twenty-four hour repeat insult testing). The test results showed an average reduction of greater than $10^6$ in bacterial count vs. untreated samples).

As there was no testing protocol available to demonstrate the efficacy of the disclosed device as it relates to its kill capabilities, the time involved, and its long term efficacy, specific test protocols were developed in relation to the disclosed device. It is well-known in the industry of life sciences, testing protocols provide individual sets of instructions that allow for the recreation of a particular laboratory experiment. Protocols provide instructions for the design and implementation of experiments that include the safety bias, procedural equipment, statistical methods, reporting and troubleshooting standards for experiments.

As disclosed herein, modifications were made to standardized test criteria (AATCC method 100 and ASTM E2149) which resulted in the development of specific protocols that allow for the evaluation and testing of the killing capability of the disclosed device over an extended time period of up to 96 hours and beyond. The modifications consisted of the use of ASTM E2149 as the base testing protocol along with AATCC method 100 applied to multiple 24-hour nonstop testing of the original sample versus a single 24-hour test period as prescribed by AATCC 100.

By way of background, the AATCC 100 test method evaluates the antibacterial properties of textiles over a 24-hour period of contact, quantitatively assessing bacteriostatic (growth inhibition) properties or bactericidal (killing of bacteria) properties associated with a textile. The method ensures continuity in approaches and replicability of results.

The ASTM E2149 method, titled "Determining the Antimicrobial Activity of Immobilized Antimicrobial Agents under Dynamic Contact Conditions" is a sensitive test. It is often used to measure the antimicrobial activity of non-leaching, irregularly shaped or hydrophobic surfaces.

With regards to efficacy, the present system has been tested against a robust organism *Staphylococcus aureus* utilizing the following recognized standards: AATCC Method 100 (modified for twenty-four hour repeat insult testing). The test results showed an average reduction of greater than $10^6$ in bacterial count vs. untreated samples).

As an example, a horse having late stage pneumonia that was expected to expire within 24 hours was treated with the disclosed dry powder and was within 24 hours healthy and pneumonia free.

The polyiodide resin powder can be mixed with a polyurethane adhesive or other suitable adhesive(s) based to form a printable ink. The ink which can be used as a coating, printed application, or as an ingredient or additive can be applied to face masks or other PPE. It is well known that PPE may include but is not limited to gloves, safety glasses and shoes, shoe covers, earplugs or muffs, hard hats, respirators, shields, coveralls, vests, surgical masks, surgical drapes, isolation gowns and full body suits.

One disclosed embodiment is a powder demand release antimicrobial contact disinfectant polyiodinated resin with the ability to be tailored to specific medical needs based on the iodine concentration of iodine in its various forms such as $I_3^-$, $I_5^-$, $I_7^-$.

The powder demand release antimicrobial contact disinfectant polyiodinated resin has been proven to maintain its kill capabilities beyond 96 hours (repeated inoculation every 24 hours with $>10^7$ *Pseudomonas aeruginosa* for the entire study) as referenced by test results done by Wuxi AppTec, a third party reference lab. The antimicrobial powder is capable of providing a high level of protection against microbes and other many biohazards, such as viruses, bacteria, fungi, and molds. In the disclosed embodiment, the polyiodinated resin particles advantageously have an average size within the range from about 5 μm to about 10 μm.

As disclosed, the polyiodide resin powder begins with a pure cationic resin which is commercially available as a chloride ($Cl^-$) as the anion. The anion exchange resin may be a whole series of possible polymers that are carbon based, but in the disclosed embodiment, the resin used is a commercially available styrene-divinylbenzene copolymer resin that has a quaternary ammonium cation as an integral part of the resin matrix. This can be described as resin with nitrogen (N) and carbon-based residues (R) attached to the resin, with the property of having a resin with a positive charge and a counter anion ($Cl^-$) with a negative charge, to end up as a neutral complex.

Typically, anion exchange resins are in the form of hydroxide ($OH^-$) or chloride ($Cl^-$). The hydroxide form can be further reacted with hydrochloric acid to form the chloride version of the resin as follows:

$$\text{Resin-NR}_4^+\text{OH}^- + \text{HCl} = \text{Resin-NR}_4^+\text{Cl}^- + \text{H}_2\text{O}.$$

This is further reacted in the presence of Iodine ($I_2$ as a mineral) and Iodide ($I^-$) salt (sodium or potassium iodide) to allow for the formation of $I_3^-$, $I_5^-$, and $I_7^-$. The initial reaction is $[I_2+I^-=I_3^-]$, which upon excess $I_2$ will react further to form $I_5^-$ as in $[I_2+I_3^-=I_5^-]$, and which upon additional excess $I_2$ will react further to form $I_7^-$ as in $[I_2+I_5^-=I_7^-]$. This is now referred to as the polyiodide resin in the disclosed system. Reactions are as follows:

$$\text{Resin-NR}_4^+\text{Cl}^- + I_3^- = \text{Resin-NR}_4^+I_3^- + \text{Cl}^-$$

$$\text{Resin-NR}_4^+\text{Cl}^- + I_5^- = \text{Resin-NR}_4^+I_5^- + \text{Cl}^-$$

$$\text{Resin-NR}_4^+\text{Cl}^- + I_7^- = \text{Resin-NR}_4^+I_7^- + \text{Cl}^-$$

Various ratios of chemicals are combined to optimize the formation of the polyiodide versions above by adding an excess of the $I_2$ and $I^-$ in appropriate proportions to substitute out the $Cl^-$ or other anions or halides based on the stoichiometry (ratio) of the reactants as given above. Multiple routes from chromatography to reactor pressures and heated fluid beds may be used to realize the end product in accordance with well-known manufacturing processes, with the variables of pressure, temperature and ratios.

The reactor operates at elevated temperatures of above room temperature to the limits of the resin's thermal stability profile temperature and at pressures of one or more atmospheres of pressure. The process can be optimized to produce a batch of any size (subject to the reactor vessel size) in a matter of hours or within one day. The total weight of iodine in the polyiodinated resin formed from the process ranges about 45% to about 70% by weight of the polyiodide complex depending on the introduction of $I_3^-$, $I_5^-$, and/or $I_7^-$. By careful control of the ratios of the Resin based Chloride version of the resin and the $I_2$ and $I^-$ ratios, mixtures ranging from the $I_3^-$ through the $I_7^-$ versions and mixtures in between can be produced. Careful control of specific ratios of reactants can yield specific versions, but are typically reaction mixtures favoring one of the polyiodides over the others. For example, if $I_3^-$ is introduced, the resulting polyiodinated resin comprises about 45% by weight of the polyiodide complex. If $I_5^-$ is introduced, the resulting polyiodinated resin comprises about 62% (by weight of the polyiodide complex. If $I_7^-$ is introduced, the resulting polyiodinated resin comprises about 69% by weight of the polyiodide complex.

The resulting polyiodide resin is then ground to about 5 μm to about 10 μm thereby forming the polyiodide resin powder. Yields at or near 100% are possible, but typically due to manufacturing loses and limits may be less than 100%.

Buffering agent can be added to maintain the desired pH, subject to the specific buffering agent that is used, in a ratio that allows for the control of the pH of the mixture in a wet environment (such as tissue or lungs) to be in the range of 3 to 7 pH units. Although any ratio of polyiodide to buffering agent can be used in the range of 10% to 100% of the polyiodide, typically the dominate agent is the polyiodide in the range of 50% to 100% of the total of the combined materials of the polyiodide styrene-divinylbenzene copolymer resin and the buffer agent.

Some examples for medical grade buffering agents that may be used are 4-(2-hydroxyethyl)-1-piperazineethanesulfonic acid (HEPES), 2-(N-morpholino)ethanesulfonic acid (MES), 3-(N-morpholino)propanesulfonic acid (MOPS) and citrates, however others may be suitable.

The disclosed method utilizes an intaglio print application methodology to create a zone of inhibition or protective barrier around a resultant PPE device. The image to be printed consists of depressions or recesses on the surface of the printing plate. The printer then covers the plate with polyiodinated ink polymer and then wipes the ink from the higher surface, leaving the depressions, or intaglio areas, filled with ink.

The gravure printing process is just one example of a printing process that may be utilized. As discussed herein, other deposition technologies could be adapted for use with the apparatus described herein. Gravure printing provides for a dot matrix inking of a printable surface. Thus, in operation, the printing matrix allows for a zone of inhibition to exist based on the size of the matrix as formed by the polyiodide inking of one or more surfaces of a personal protective device or equipment.

The printable ink comprises polyiodide resin powder mixed with a polyurethane adhesive or other suitable adhesive(s) based on the requirements of the particular device to be treated. The ratio of iodinated powder to polyurethane adhesive and particle size can be adjusted to meet the needs of the surface to be printed. Color can be added when needed by the use of a dye added to the overall mix.

The disclosed method comprises the application of the polyiodinated ink polymer to one or more surfaces of PPE including but not limited to face masks, a surgical masks, caps, isolation gowns, shoe covers, surgical drapes, gloves, respirators and the like using an intaglio printing process. The application of the polyiodinated ink to PPE creates a polyiodide resin-enhanced apparatus which creates a molecular sub-microscopic "cloud of protection" between the apparatus and the user. The resultant PPE device provides for a direct contact kill of bacteria, fungi and viruses causing respiratory tract infections originating from bacterial, fungal and viral agents.

Again, other deposition-type printing processes may be utilized depending on the particular application desired. A particular intaglio printing or similarly-controlled ink deposition process may be utilized to accommodate the depth and matrix pattern of depressions to optimize control of the antimicrobial protection desired.

The antimicrobial substrate PPE printing process comprises engraving a cylinder with one more or images, thereby creating one or more recessed cells to contain a transferable ink; partially immersing the engraved cylinder in an ink tray to fill the one or more recessed cells; allowing the engraved cylinder to rotate and draw excess ink onto its surface and into the one or more recessed cells; scraping the engraved cylinder with a blade before the cylinder makes contact with a surface of a printable substrate, thereby removing excess ink from non-recessed areas adjacent the one or more recessed cells; positioning the substrate between an impression roller and the engraved cylinder; applying a force so as to bring the substrate into contact with the engraved cylinder, whereby ink is transferred from the recessed cells and onto the substrate to form an inked substrate; and drying the inked substrate.

When the inked substrate goes through a dryer, it must be completely dry before going through the subsequent inking steps that may be required to produce a final image.

Generally, an image (in this application, a matrix of depressions) is acid-etched on the surface of a metal cylinder. The cylinder consists of a pattern of cells that are recessed into the cylinder surface. The pattern of cells on the etched cylinder makes up the dot matrix required for the overlapping zone of inhibition needed for maximum coverage of the antimicrobial ink onto the PPE substrate and can vary in size and shape as required to achieve the desired antimicrobial coverage from the antimicrobial ink. In addition, the etched cylinder may comprise recessed cells of different depths depending on the desired antimicrobial coverage.

The width of a cylinder is selected so as to accommodate the width of woven fabric or non-woven scrim (called the substrate) that is required to be printed with the iodinated polymer polyurethane ink. As will be appreciated by one having ordinary skill in the art, cylinder width will vary. For example, scrim (non-woven textile) required for a face mask or for isolation gowns may come in 16-inch wide rolls. As another example, surgical drapes may require 48-inch wide rolls of scrim. In any case, the disclosed method and device can accommodate variable substrate sizes. Various concentrations of the polyiodide in the ink can be used to achieve specific outcomes.

The recessed cells hold the ink (iodinated polymer) that is transferred to the target PPE substrate. The precision of the dimensions of the cells correlates to the antimicrobial effectiveness of the PPE device. Deeper cells comprise a higher concentration of antimicrobial polyiodide ink than shallow cells. Thus, deeper cells can provide longer antimicrobial protection if required.

The recessed cells are filled with ink and the non-printing portions of the cylinder are wiped with a doctor blade or scraped to remove the excess. The substrate is then pressed against the inked cylinder on a rotary press, and the image is transferred directly to the PPE substrate. The engraved cylinder sits partially immersed in an ink fountain/well containing the iodinated polymer adhesive mixture, where it picks up ink to fill its recessed cells on each rotation of the press. A final drying stage comprising warm air can be used to set the iodinated polymer/polyurethane ink mixture printed on the substrate.

In one embodiment, a 16" wide non-woven scrim used in the construction of isolation gowns of an approximate 0.015" thickness was used. A 16" Gravure roller was etched using a dot matrix spacing of 0.030". Although a cell depth of 0.020" was utilized, it was contemplated that the cell depth of the etched roller could be adjusted to increase or decrease the amount of ink deposited as needed. The matrix spacing can similarly be varied to achieve the required antimicrobial performance.

The ink was a mixture of 25.8% 10 micron iodinated polymer with the remainder comprising 9% polyurethane adhesive and 65.2% water mixture. The ink mixture was formulated at 23° C. (73° F.) which was considered to be room temperature. The ink well of the printer bed was filled with the aforementioned iodinated polymer ink mixture.

The non-woven scrim was fed into the roller and the roller was rotated by a hand crane to advance the scrim and to transfer the ink to the surface of the scrim. The scrim was allowed to air dry. After drying, test samples were cut from the printed scrim and tested for antimicrobial performance. The goal was to obtain a 4 log or greater kill of the organisms tested.

Tested organisms comprise *Pseudomonas aeruginosa* and *Staphylococcus aureus*. Test results for SARS (SARS-CoV-1) and Coronavirus (SARS-CoV-2) are expected to be better compared to the most robust *Pseudomonas aeruginosa* and *Staphylococcus aureus*.

The disclosed system provides for a PPE device capable of sustained kill of organisms for up to 96 hours. In addition, the disclosed system creates a molecular sub-microscopic "cloud of protection" from bacterial, fungal and viral agents. Further, the disclosed system provides a PPE device capable of direct contact kill of organisms.

The invention claimed is:

1. A method of providing polyiodide resin powder-enhanced personal protective equipment (PPE) capable of creating a protective barrier around the PPE for a direct contact kill of bacteria, fungi and viruses, the method comprising the steps of:
   reacting a cationic resin having a positive charge and an anion having a negative charge in the presence of iodine ($I_2$ as a mineral) and Iodide ($I^-$) salt to allow for the formation of $I_3^-$, $I_5^-$, and $I_7^-$ thereby forming a polyiodide resin having a total weight of iodine ranging from about 45% to about 70% by weight of polyiodide complex depending on the introduction of $I_3^-$, $I_5^-$, and/or $I_7^-$;
   processing said polyiodide resin to form a polyiodide resin powder having a mesh size of about 1 μm to about 150 μm;
   mixing said polyiodide resin powder with an adhesive to form a printable polyiodinated ink polymer;
   depositing said printable polyiodide ink onto or into one or more surfaces of PPE to create a polyiodide resin-enhanced apparatus that enables sub-microscopic protection between the apparatus and a user.

2. The method of claim 1, wherein the deposition step comprises partially immersing an engraved cylinder having one or more recessed cells in an ink tray containing said printable polyiodide ink to fill the one or more recessed cells; allowing the engraved cylinder to rotate and draw ink onto its surface and into the one or more recessed cells; scraping the engraved cylinder with a blade before the cylinder makes contact with a surface of a printable PPE substrate, thereby removing excess ink from non-recessed areas adjacent the one or more recessed cells; positioning the PPE substrate between an impression roller and the engraved cylinder; applying a force so as to bring the substrate into contact with the engraved cylinder, whereby said printable ink is transferred from the recessed cells and onto the substrate to form an inked substrate.

3. The method of claim 2 further comprising the step of drying the inked substrate before going through subsequent inking steps that may be required to produce a final product.

4. The method of claim 2 further comprising the step of adjusting the size, depth, pattern or a combination of the one or more recessed cells to create a desired zone of inhibition formed by the polyiodide ink to optimize a detriment to bacterial, fungal and viral organisms.

5. The method of claim 1 further comprising the step of verifying the polyiodide resin-enhanced apparatus enables a sustained kill of organisms for up to 96 hours.

6. The method of claim 1, wherein the deposition step further comprises utilizing intaglio printing, 3D printing, offset lithography, flexography, digital printing, large format printing, screen printing or LED UV printing.

7. The method of claim 6 further comprising the step of verifying the polyiodide resin-enhanced apparatus enables a sustained kill of organisms for up to 96 hours.

8. A method of applying a polyiodinated ink polymer comprising polyiodide resin powder to one or more surfaces of a respective personal protective device or PPE to enable an immediate contact kill to bacterial, fungal and viral infections that may affect the lungs of a mammal, the method comprising the steps of:
   providing a cationic resin comprising a positive charge and an anion with a negative charge;
   reacting the cationic resin in the presence of iodine ($I_2$ as a mineral) and Iodide ($I^-$) salt to allow for the formation of $I_3^-$, $I_5^-$, and $I_7^-$ thereby forming a polyiodide resin having a total weight of iodine ranging from about 45% to about 70% by weight of polyiodide complex depending on the introduction of $I_3^-$, $I_5^-$, and/or $I_7^-$;
   processing said polyiodide resin to form a polyiodide resin powder having a mesh size of about 1 μm to about 150 μm;
   adding a buffering agent to enable the pH of the polyiodide resin powder to be maintained in a ratio that allows for the control of the pH of the mixture in a wet environment, thereby forming a buffered polyiodide resin powder;
   mixing said buffered polyiodide resin powder with an adhesive to form a printable polyiodinated ink polymer;
   depositing said polyiodide ink polymer using an intaglio printing application onto or into one or more surfaces of PPE to create a polyiodide resin-enhanced apparatus that enables a zone of protection between the apparatus and a user.

9. The method of claim 8 further comprising the step of verifying the polyiodide resin-enhanced apparatus enables a sustained kill of organisms for at least 96 hours.

10. A polyiodide resin powder-enhanced PPE apparatus capable of creating a protective barrier around the apparatus for a direct contact kill of bacteria, fungi and viruses, the apparatus comprising:
    an item worn to minimize exposure to hazards that cause injuries and illnesses, the item treated with a polyiodide resin powder having a total weight of iodine ranging from about 45% to about 70% by weight of polyiodide complex depending on the introduction of $I_3^-$, $I_5^-$, and/or $I_7^-$;
    the polyiodide resin powder having a mesh size of about 1 μm to about 150 μm; and
    wherein the polyiodide resin powder further comprises a buffering agent to allow the polyiodide resin powder to be maintained at a desired pH in a ratio that allows for the control of the pH of the mixture in a wet environment.

11. The apparatus of claim 10 being capable of a sustained kill of organisms for at least 96 hours.

12. A polyiodide resin powder-enhanced PPE apparatus having a protective barrier formed around the apparatus so as to eliminate the risk of a user contracting illnesses originating from bacterial, fungal and viral agents, the apparatus comprising:
    an item worn to minimize exposure to hazards that cause injuries and illnesses, one or more surfaces of said item having a polyiodinated ink polymer deposited thereon, the ink polymer comprising an adhesive and a polyiodide resin powder having a total weight of iodine ranging from about 45% to about 70% by weight of polyiodide complex depending on the introduction of $I_3^-$, $I_5^-$, and/or $I_7^-$;

the polyiodide resin powder having a mesh size of about 1 µm to about 150 µm; and wherein the ink polymer is deposited on said item by means of a print application.

13. The apparatus of claim 12, wherein the print application comprises utilizing intaglio printing, 3D printing, offset lithography, flexography, digital printing, large format printing, screen printing or LED UV printing.

14. The apparatus of claim 12, wherein the print application comprises partially immersing an engraved cylinder having one or more recessed cells in an ink tray containing said printable polyiodide ink to fill the one or more recessed cells; allowing the engraved cylinder to rotate and draw ink onto its surface and into the one or more recessed cells; scraping the engraved cylinder with a blade before the cylinder makes contact with a surface of a printable PPE substrate, thereby removing excess ink from non-recessed areas adjacent the one or more recessed cells; positioning the PPE substrate between an impression roller and the engraved cylinder; applying a force so as to bring the substrate into contact with the engraved cylinder, whereby said printable ink is transferred from the recessed cells and onto the substrate to form an inked substrate.

15. The apparatus of claim 14, wherein the print application further comprises drying the inked substrate before going through subsequent inking steps that may be required to produce a final product.

16. The apparatus of claim 14, wherein the one or more recessed cells when filled with polyiodide ink creates a zone of inhibition, the zone being adjustable in size, depth, pattern or a combination thereof as required to achieve a desired antimicrobial coverage.

17. The apparatus of claim 12, wherein the polyiodide resin powder further comprises a buffering agent to allow the polyiodide resin powder to be maintained at a desired pH in a ratio that allows for the control of the pH of the mixture in a wet environment.

18. The apparatus of claim 17, wherein the desired pH ranges from about 3 to about 7.

19. The apparatus of claim 17, the ratio of polyiodide to buffering agent ranges from about 50% to about 100% of the total of the combined materials of the cationic resin and the buffering agent.

20. The apparatus of claim 12 being capable of a sustained kill of organisms for up to 96 hours.

21. A method of applying a polyiodinated ink polymer comprising polyiodide resin powder to one or more surfaces of a respective personal protective device or PPE to enable an immediate contact kill to bacterial, fungal and viral infections that may affect the lungs of a mammal, the method comprising the steps of:

providing a cationic resin comprising a positive charge and an anion with a negative charge;

reacting the cationic resin in the presence of iodine ($I_2$ as a mineral) and sodium or potassium iodide to allow for the formation of $I_3^-$, $I_5^-$, and $I_7^-$ thereby forming a polyiodide resin having a total weight of iodine ranging from about 45% to about 70% by weight of polyiodide complex depending on the introduction of $I_3^-$, $I_5^-$, and/or $I_7^-$;

processing said polyiodide resin to form a polyiodide resin powder having a mesh size of about 1 µm to about 150 µm;

adding a buffering agent to enable the pH of the polyiodide resin powder to be maintained in a ratio that allows for the control of the pH of the mixture in a wet environment, thereby forming a buffered polyiodide resin powder;

mixing said buffered polyiodide resin powder with an adhesive to form a printable polyiodinated ink polymer;

depositing said polyiodide ink polymer using an intaglio printing application onto or into one or more surfaces of PPE to create a polyiodide resin-enhanced apparatus that enables a zone of protection between the apparatus and a user.

* * * * *